United States Patent [19]
Bloch

[11] 3,953,898
[45] May 4, 1976

[54] PROSTHETIC ONE-WAY HEART VALVE

[76] Inventor: Eric Bloch, 556 W. 141st St., New York, N.Y. 10031

[22] Filed: June 6, 1975

[21] Appl. No.: 584,435

[52] U.S. Cl. ................................. 3/1.5; 137/527.8
[51] Int. Cl.² .......................................... A61F 1/22
[58] Field of Search ................................ 3/1.5, 1; 137/527–527.8

[56] References Cited
UNITED STATES PATENTS

| | | | |
|---|---|---|---|
| 3,445,863 | 5/1969 | Wada | 3/1.5 |
| 3,448,465 | 6/1969 | Pierce et al. | 3/1.5 |
| 3,476,143 | 11/1969 | Kaster | 3/1.5 X |
| 3,513,485 | 5/1970 | Davila | 3/1.5 |
| 3,546,711 | 12/1970 | Bokros | 3/1.5 |
| 3,903,548 | 9/1975 | Nakib | 3/1.5 |

*Primary Examiner*—Ronald L. Frinks
*Attorney, Agent, or Firm*—Alan H. Levine

[57] ABSTRACT

A heart valve including a generally annular body and a disc within the body pivotable about a centerline of the disc. Vanes project from one face of the disc in a direction opposite the flow direction through the valve, fluid flow against the vanes causing the valve to open. A baffle extends across the body adjacent the face of the disc opposite the face from which the vanes project, the baffle directing fluid flowing in the no-flow direction of the valve against the disc so as to close the valve. The disc portions on opposite sides of the pivot axis are of substantially equal size and weight. The disc is limited to pivoting through an acute angle, and in certain embodiments may also rotate in its own plane. The vanes may be arranged on only one half the disc, or symmetrically on the entire disc, and the vanes are preferably spaced apart to define openings between them to accommodate fluid flow. A second baffle may extend across the body adjacent the face of the disc from which the vanes project.

16 Claims, 15 Drawing Figures

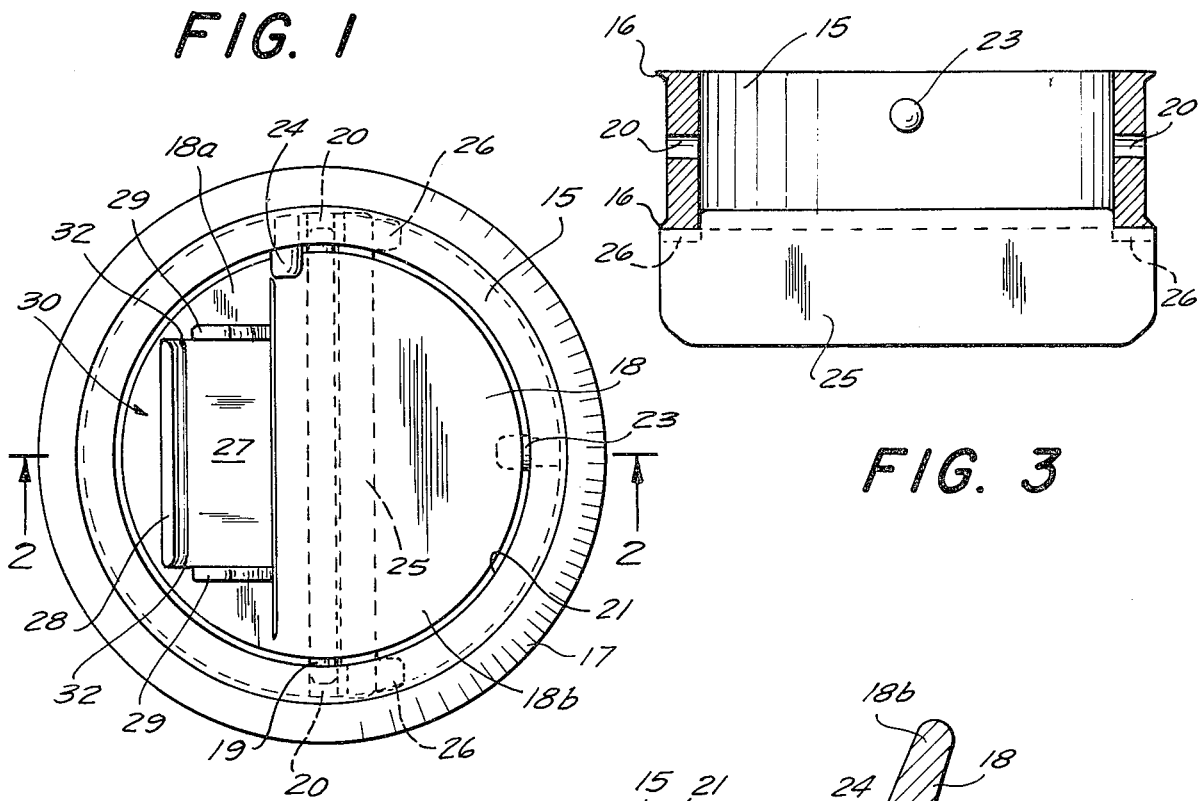
FIG. 1
FIG. 3
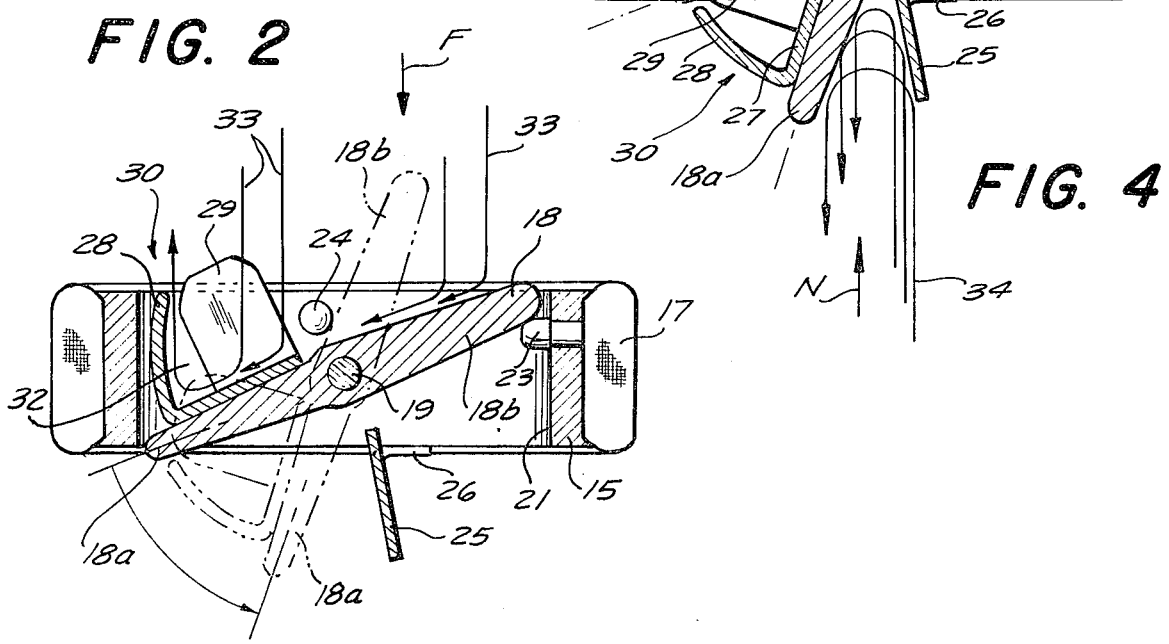
FIG. 2
FIG. 4

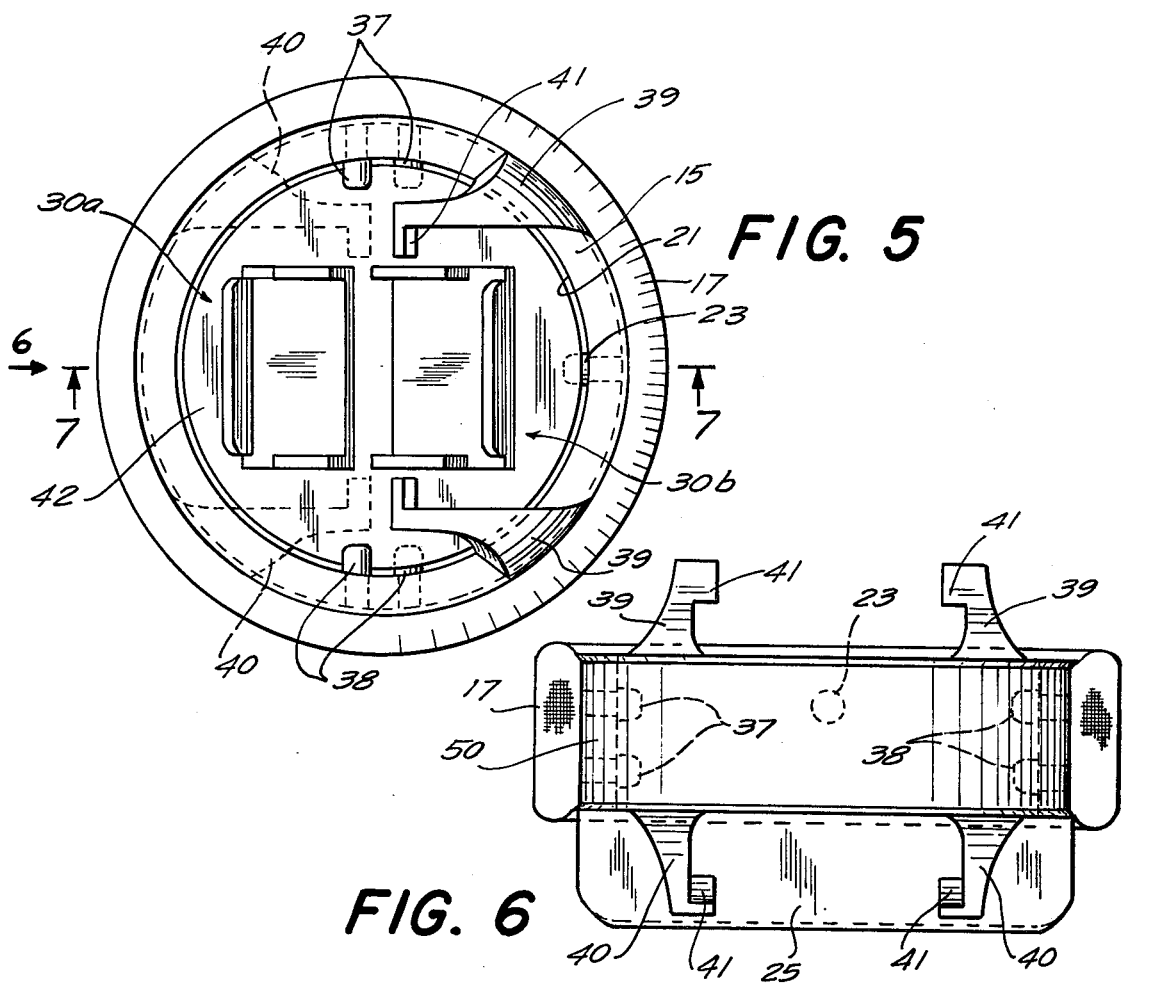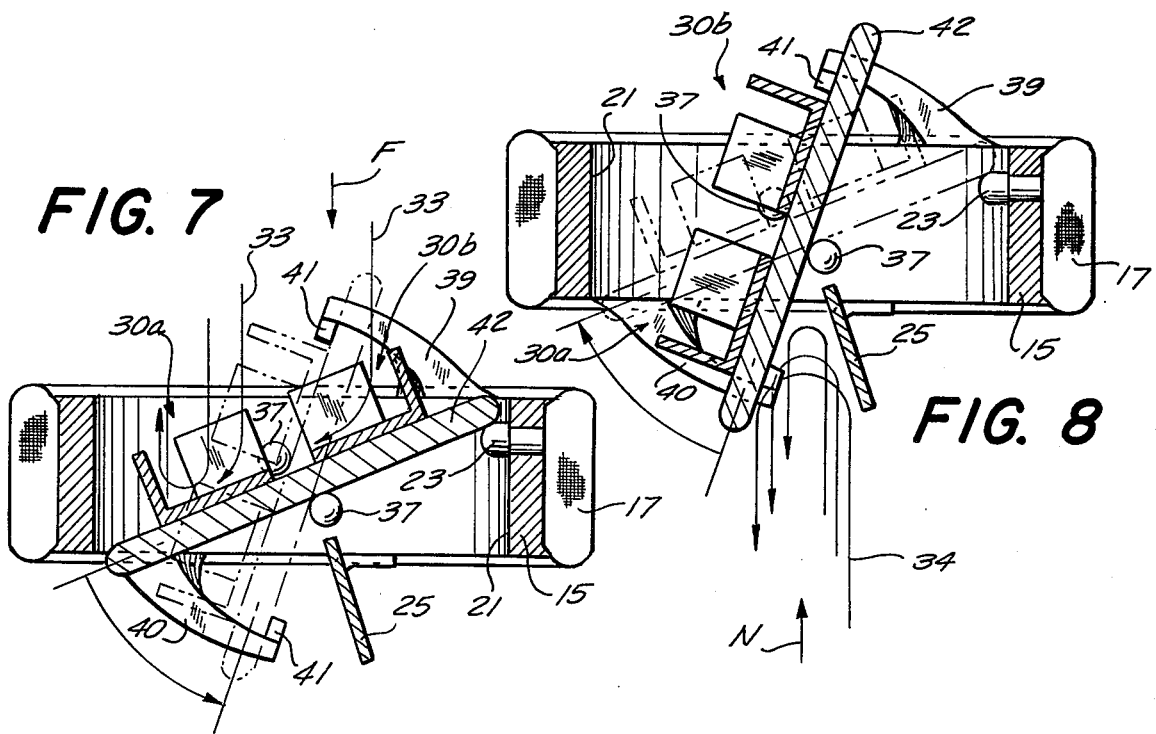

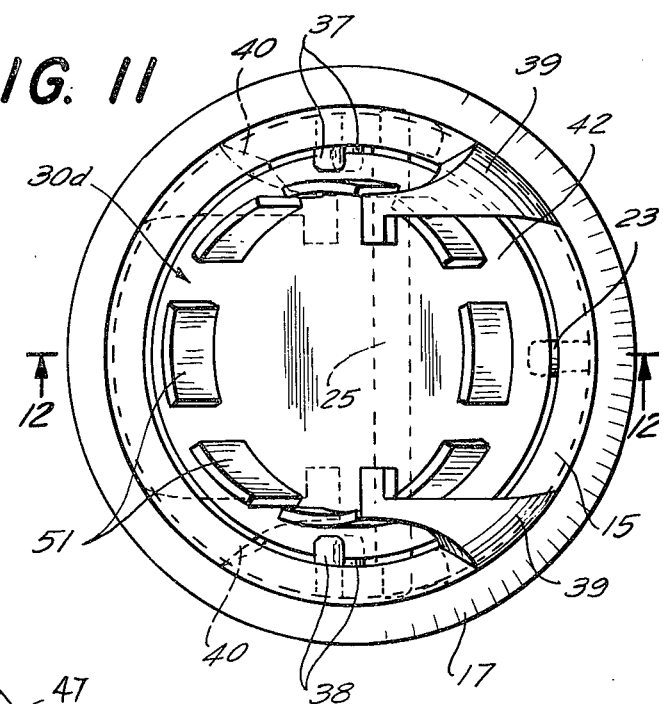
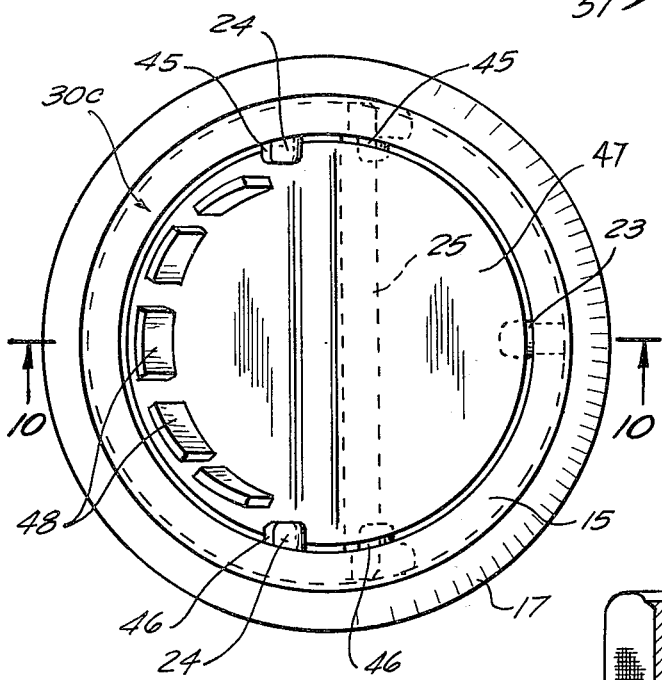
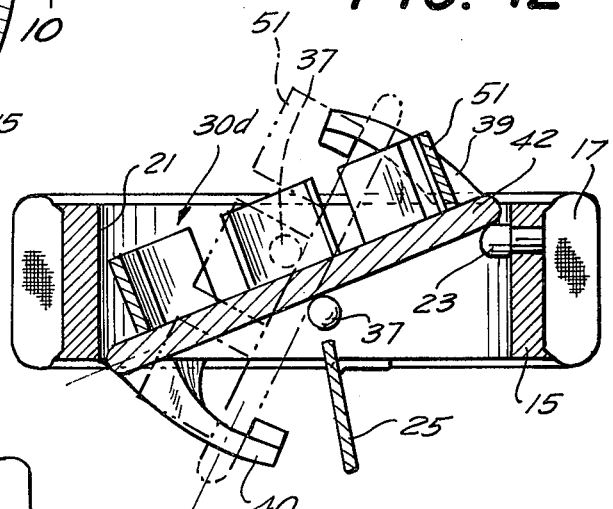
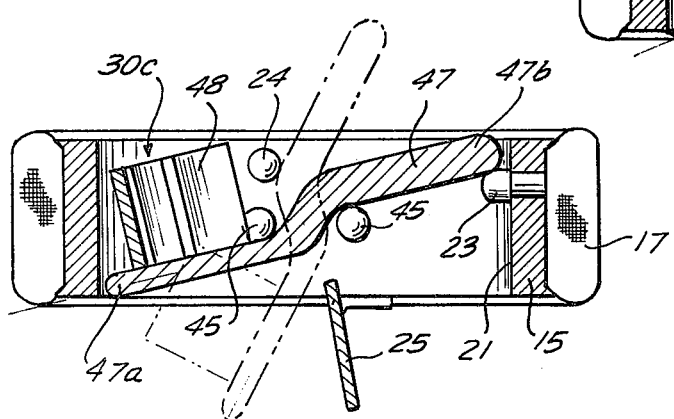

PROSTHETIC ONE-WAY HEART VALVE

The present invention relates to an improved one-way heart valve and more particularly to an artificial cardiac valve of the pivoting disc type for implanting into a human heart as replacement for diseased or malfunctioning valves.

A number of different types of artificial heart valves are available and of these the most commonly used are the ball or cage type valve and the pivoting leaf or disc type valve. The pivoting disc valve is at present the most used and preferred valve on account of its simple design and mechanism.

However, a number of deficiencies are recognized in the existing disc heart valves, which result from certain innate working limitations which restrict their usefulness. The design of a pivoting disc valve must take into consideration the fact that the opening thrust force of the flowing blood opposes the closing thrust force of the flowing blood, to which the two wings of the disc plate are subjected by the blood stream.

To overcome the obstacle of the opposing forces and to avoid a stalemate, the pivoting axis of the disc is located off-center. It is evident that in this way, the pressure of the blood acting against both wings of the disc, will cause the wing with the larger area to overpower the smaller wing and turn the larger wing in the direction of the flow of the blood and thus open the valve. If the blood changes its flow to the opposite direction, the same procedure will take place and the valve will be closed.

The off-center pivoting axis line usually divides the pivoting disc into a ⅓ area and a ⅔ area and it is obvious that the ⅔ area is twice as heavy in weight and inertial resistance as the opposing ⅓ area. The average weight and inertial resistance of a heart valve disc is approximately 23 grains. If it is considered that the valve seat of the orifice will be struck by the valve disc approximately 40 million times during the period of one year, 23 grains, the weight of a disc, multiplied by 40 million produces 131,430 lbs., which means ⅓ of the disc weight is 43,810 lbs. and ⅔ of the disc weight is 87,620 lbs. The weight of the smaller ⅓ wing, by way of balancing, assists in lifting the larger ⅔ wing of the disc, when the heart is closing the valve. Therefore 43,810 lbs. can be deducted from 87,620 lbs. which results in an unbalanced load of 43,810 lbs. This is the actual load, or better expressed inertial resistance, which the heart, a muscle the size of a fist, has to lift and to overcome, in order to close a present day disc valve, pivoting on an axis located ⅔ off centerline during a 1 year period.

In reality the workload of the heart is even larger than the above-mentioned figure, because the balancing weight of the smaller wing of the disc is much less than ⅓ of the overall weight of the pivoting disc. This is due to the curvature of the disc circumference which reduces considerably the area of the smaller wing and therefore its weight. Thus the remaining area and weight of the almost rectangular center section of the disc, which is actually the unbalanced load which has to be lifted by the heart, is much larger and heavier, as stated previously, and it can be safely assumed that this amounts to an additional weight of approximately 15,000 lbs. per year which must be lifted by the heart.

If, in this connection, the performance of the ball type valve is examined, it is found that the dynamic inertia of the flow regulating mechanism or ball valve member, is even of a still greater disadvantage than that of the off center tilting disc valve. In the construction of a ball type valve there is no balancing force available to assist the heart in lifting the ball valve member to close the valve. The heart must lift and move the entire ball and its full inertial resistance. The average weight of a ball valve member is approximately 49 grains. This weight multiplied by 40 million amounts to 280,000 lbs. and this is the work the heart has to do in order to close a ball type heart valve in the period of 1 year. The heart has only one job to do: it must pump blood. The heart can be studied at present as an engineer would examine a water pump. Its work can be measured and expressed in the physical terms of the output of the fluid (blood) times the pressure : $W$ (work)$=V \times P$ (volume times pressure). This physical formula applied in laboratory tests has established that the average stroke work produced by the natural heart of a 70 kg. man is 1.2 joules or 10.3 inch-pounds.

It is evident that these figures are only valid for pumping of blood by a heart having its natural healthy heart valves. When an artificial heart valve is implanted in a patient, his heart, in addition to its regular workload of pumping blood, also has to perform the job of closing the disc of the artificial valve. This closing of the artificial heart valve involves a significant additional work load, which the heart must now perform on top of its regular function. There are many cases found in postoperative patients where this additional and substantial work load generated an abnormal pressure gradient, which was very injurious to the health and ultimately the life of these patients.

A great deal of work has been done in many centers, for many years, with the aim of designing the ideal type of an artificial heart valve, but so far no construction has been satisfactory enough to be considered as the conclusive solution. One of the biggest obstacles to success is the additional force needed by the artificial heart valves of previous constructions, a force which the heart must produce in order to operate these valves. The most important characteristic of the ideal type of an artificial heart valve is that it be absolutely efficient, which means it should permit the free flow of blood, equal to the amount delivered by a natural heart valve, without imposing on the heart any additional work load. Therefore, the ball type heart valve and the off center pivoting disc valve of previous constructions incorporate some significant disadvantages in their design and cannot be regarded as the definitive solution to construction of the ideal artificial heart valve.

Another very important attribute of the ideal artificial heart valve is that it should protrude as little as possible into the ventricle. The ventricle is pretty much filled with muscle and fibrous tissue and there is always the danger that a valve mechanism protruding too far into the ventricle might get caught and stuck. The ball type valve protrudes very far into the ventricle and the oscillating disc valve, with an off center pivoting disc, also projects considerably into the heart chamber when the larger wing of the disc is tilted into open position.

A further very important consideration is that the effectiveness of an artificial heart valve is dependent upon a swift reaction time during operation. On account of the off center tilting of the disc of a pivoting disc valve, the larger wing of the disc must describe a relative longer circular movement during the opening and closing of the valve than the shorter wing of the disc. This means that the reaction time of the valve is considerably increased, because the larger wing of the disc must travel a longer distance.

Still another important feature of an artificial heart valve is that the opening of the cylindrical valve body should allow the blood stream to flow freely and without obstruction. When the valve disc pivots about an off-center line, it has been found that the narrower part of the orifice fills up with blood sediments which make the blood passage more and more narrow, plug up the flow channel in the course of time, and even cause hemolysis.

All these outlined conditions are significant disadvantages which are overcome by the present invention.

It is a principal object of this invention to provide a prosthetic heart valve incorporating a pivoting disc of such a design that the pivot axis line is located in the center of the disc, dividing it into two wings of equal area and inertial resistance, the two wings keeping each other in balance and thus eliminating the necessity for the heart to use a substantial additional pumping force to move the disc into closed position.

It is a further object of this invention to provide a prosthetic heart valve comprising a disc which tilts around a pivot axis line located in the center of the disc, thus dividing the valve disc into two wings of equal size so that when the valve is in open position, the wing of the disc turned into the direction of flow of the blood stream protrudes much less far into the ventricle, as compared with the larger wing of a disc which has an off-center pivoted axis line. Thus, the present invention reduces considerably the risk that the wing of the disc protruding into the ventricle may get stuck.

Another important feature of this invention is that since it employs a valve disc which pivots around a center line axis, this design reduces considerably the length of the arc of travel of each wing during the opening and closing operation, as compared to the length of the arc of movement of the larger wing when the pivot axis is located off-center. Thus the reaction and response time of the present valve is more rapid and more instantaneous as compared with existing constructions.

A further important feature of this invention is that due to the valve disc pivoting on its centerline, the flow passage of the valve body is divided into two openings of equal size, thus allowing the blood stream to flow freely and without restriction.

It is still another object of this invention to provide a heart valve of very simple operation and which is therefore a safe mechanism.

Briefly stated this invention is a one-way valve characterized by the construction comprising an annular valve body which has an opening therein allowing fluid to flow through the valve. A thin disc-type valve member is located inside the valve body and is pivotably mounted on the valve body by shaft means which permit the disc to swing around its center line axis for opening and closing purposes.

In accordance with an alternative embodiment of this invention the pivoting disc is not connected to the valve body by shaft means, but is held in assembled relation to the valve body by connecting means which cause the disc to pivot around its center line axis, but this axis is only an imaginary chord which does not exist and therefore the disc is allowed to float during operation.

A still further embodiment of this invention makes it possible for a disc, which is pivoting around its center line axis on an imaginary chord, to simultaneously float and rotate freely in its horizontal plane while the valve is operating.

Additional objects and advantages of the invention will be apparent from the following description, in which reference is made to the accompanying drawings.

In the drawings:

FIG. 1 is a plan view of a prosthetic one-way heart valve according to the present invention, the valve being shown in closed condition;

FIG. 2 is a vertical cross-sectional view taken along line 2—2 of FIG. 1;

FIG. 3 is a vertical cross-sectional view taken in a direction perpendicular to the line 2—2, the disc and suture ring being removed for clarity;

FIG. 4 is a view similar to FIG. 2, the valve being shown in open condition in solid lines;

FIG. 5 is a plan view of a second embodiment of the present invention, the valve being shown in closed condition;

FIG. 6 is an elevational view of the valve looking in the direction of arrow 6 of FIG. 5, a portion of the suture ring being removed;

FIG. 7 is a vertical cross-sectional view taken along line 7—7 of FIG. 5;

FIG. 8 is a view similar to FIG. 7, the valve being shown in open condition in solid lines;

FIG. 9 is a plan view of a third embodiment of the present invention, the valve being shown in closed condition;

FIG. 10 is a vertical cross-sectional view taken along line 10—10 of FIG. 9;

FIG. 11 is a plan view of a fourth embodiment of the present invention, the valve being shown in closed condition;

FIG. 12 is a vertical cross-sectional view taken along line 12—12 of FIG. 11;

Figure 13:
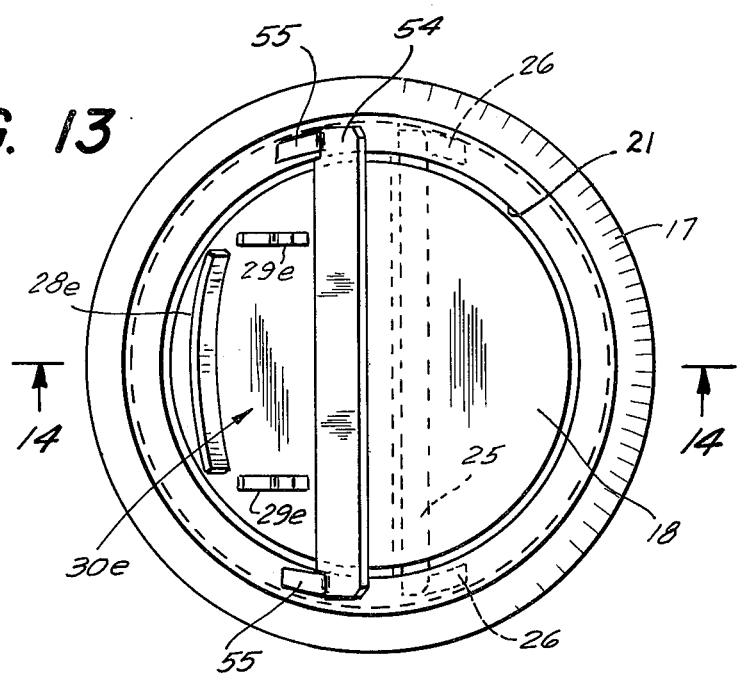
FIG. 13 is a plan view of a fifth embodiment of the present invention, the valve being shown in closed condition.

One embodiment of a prosthetic one-way heart valve chosen to illustrate the present invention, and shown in FIGS. 1–4, includes an annular valve body 15 having outwardly projecting peripheral ridges 16 at each end. Surrounding body 15, between ridges 16, is a ring of needle-pierceable material 17, such as a suitable textile, by means of which the valve may be sutured into a heart. Body 15 has a central opening 21 defining a blood flow passageway, and a disc 18 is pivotally arranged within the opening for controlling the flow of blood through the valve.

Disc 18 is a flat element having a hole extending diametrically through it. A shaft 19 is accommodated within the hole, the ends of the shaft extending beyond the periphery of disc 18 into holes 20 provided at diametrically opposed points in valve body 15. Shaft 19 defines the pivot axis of disc 18, the pivot axis extending along the centerline of the disc thereby dividing the latter into two portions 18a and 18b of equal size and of the same, generally semi-circular, shape.

If central opening 21 is circular, disc 18 may also be circular, but will preferably be slightly elongated or elliptical, the elongation or major axis of the ellipse being in a direction perpendicular to shaft 19. By means of an elliptical shape, disc 18 will be equidistantly spaced from body 15 along its entire periphery when the disc is in its closed position (FIGS. 1 and 2) wherein it is tilted with respect to the plane of body 15.

Extending into the central opening 21 of the valve body 15 from its inner surface is an abutment 23 defining the position of disc 18 in the closed condition of the valve, as shown in FIG. 2. Another abutment 24, projecting inwardly from the inner surface of body 15, defines the position of disc 18 in the open condition of the valve, as shown in FIG. 4. Extending across the central opening of body 15 at the downstream end of the body, and parallel to shaft 19, is a baffle plate 25. Baffle plate 25 is slightly spaced from a diameter of body 15 toward disc portion 18b. Portions of the ends of baffle plate 25 are bent at an acute angle to the remainder of the baffle plate defining tabs 26 which are welded or otherwise permanently secured to body 15.

Fixed to one face of disc portion 18a are vane means furnished in the form of a piece of sheet metal bent to define a base 27, and three upstanding fins or ridges 28 and 29 projecting generally upstream, i.e., in a direction opposite to the flow direction through the valve. As may be seen clearly in FIG. 1, side ridges 29 extend perpendicular to central ridge 28, the three ridges defining a pocket-like arrangement 30 for catching blood flowing against disc 18, as will be described in more detail below.

Each of the ridges 29 is preferably spaced from the ridge 28 to leave openings 32 through which blood flowing into the pocket can leave. The pocket is, therefore, self-cleaning, and openings 32 also prevent the formation of blood clots within the pocket. Similarly, it will be noted that the periphery of disc 18 is spaced slightly from the inner surface of valve body 15 when the valve is closed, so as to prevent disc 15 from becoming wedged in a closed condition.

Abutment 23 is so placed that when the valve is closed (FIG. 2), disc 18 is arranged at a relatively small acute angle to the plane of valve body 15. Abutment 24 is so positioned that when the valve is open (FIG. 4), disc 18 is arranged at a relatively large acute angle to the plane of valve body 15. Thus, the positioning of abutments 23 and 24 is such that disc 18 pivots during its entire movement through an acute angle. Baffle plate 25 is arranged at an acute angle to the plane of valve body 15 on the disc portion 18b side of the valve body.

As may be seen clearly in FIGS. 2 and 4, disc portion 18a has a reduced thickness as compared to disc portion 18b so as to compensate for the weight added to disc portion 18a by the pocket 27–29. As a result, disc portion 18a and the pocket 30 which it carries are of substantially equal weight to disc portion 18b.

In operation, when the valve is in the closed position shown in solid lines in FIG. 2, blood indicated by the arrows 33 flowing toward the valve in the flow direction (arrow F) of the valve, strikes disc 18. Due to the angled condition of the disc, the blood flows along the disc surface into pocket 30. Blood flow against the ridges 28 and 29 of the pocket, especially ridge 28, produces a turbine effect and swings disc 18 to its open position, shown in broken lines in FIG. 2. The central opening of body 15 is thereby opened wide permitting blood to flow easily through the opening on both sides of disc 18.

Upon reverse flow of the blood indicated by arrows 34 in FIG. 4 in the no-flow direction (arrow N) of the valve, the blood flows into an inverted V-shaped pocket defined by baffle plate 25 and disc portion 18a. As a result, disc 18 is swung from the solid line position of FIG. 4 to the broken line position, thereby closing the valve and preventing flow through the valve in the direction indicated by arrow N.

All the parts of the valve just described, and the valves to be described below, except for suture ring 17, may be formed of stainless steel or any other suitable material inert to blood and body tissue. Suture ring 17 may be formed of a knitted or woven nylon, or any other suitable inert material.

It will be appreciated that since disc portions 18a and 18b are of substantially equal weight, very little force is required to swing disc 18 between its open and closed positions. Consequently, employment of this valve adds very little to the work which the heart must do. Furthermore, since disc portions 18a and 18b are of substantially equal size, neither portion projects excessively into the heart cavities, and the flow areas through the valve body central opening 21 on both sides of pivot axis 19 are of maximum size to prevent clogging.

Another embodiment of the invention is illustrated in FIGS. 5–8. This embodiment is similar to the valve described above in that it has an annular valve body 15 surrounded by a suture ring 17 and provided with a baffle plate 25 and an abutment 23. In addition, valve body 15 is provided with two pairs of protrusions 37 and 38, projecting into the central opening 21 from the inner surface of valve body 15, the protrusions 37 and 38 being arranged at diametrically opposed locations on the valve body.

Valve body 15 also carries two pairs of fingers 39 and 40 each finger being formed at its free end with a stop 41. Whereas abutment 23 defines the position of the valve disc in the closed condition of the valve, stops 41 define the position of the disc in the open condition of the valve.

Valve disc 42 differs from disc 18 of FIGS. 1–4 in that it is not mounted on a shaft. Instead, the peripheral edge of disc 42 fits loosely between each pair of protrusions 37 and 38. The protrusions thereby support disc 42 for pivotal movement. Fingers 39 and 40 also serve to position disc 42 and prevent it from falling out of body 15.

An advantage of pivotally supporting disc 42, as shown in FIGS. 5–8, as compared to the shaft support of disc 18 in FIGS. 1–4, is that disc 42 is able to rotate in its own plane as well as pivot between open and closed positions. This helps the valve to be continuously self-cleaned as blood flows through it. For this purpose, disc 42 must be circular, not elliptical.

Since disc 42 is rotatable in its own plane, it is provided with two pocket members 30a and 30b symmetrically arranged with respect to any diameter of the disc. Thus, regardless of the position to which disc 42 rotates in its own plane, there will always be a pocket into which blood flow indicated by the arrows 33 will be directed so as to swing disc 42 from its closed position, shown in solid lines in FIG. 7, to its open position shown in broken lines in FIG. 7. Disc 42 is swung from its open position shown in solid lines in FIG. 8, to its closed position, shown in broken lines, by reverse blood flow indicated by arrows 34, as was described above with respect to FIG. 4. In its open position, disk 42 permits flow through the valve in the direction of arrow F, and in its closed position, disk 42 prevents flow through the valve in the direction of arrow N.

Although disc 42 rotates in its own plane, the pivot axis always substantially coincides with a centerline or diameter of the disc. Furthermore, since two symmetrically arranged pockets 30a and 30b are provided the disc portions on both sides of the pivot axis are always balanced.

A further embodiment of the invention is illustrated in FIGS. 9 and 10. This valve includes, as before, an annular body 15, suture ring 17, baffle plate 25, and abutments 23 and 24. Body 15 is also provided with two pairs of inwardly-directed, diametrically opposed protrusions 45 and 46 for pivotally supporting a valve disc 47.

As best seen in FIG. 10, disc 47 is bent twice in opposite directions near one of its diameters so as to give it an elongated S cross-sectional shape defining two parallel but offset portions 47a and 47b. Disc portion 47a carries a pocket 30c defined by a series of upstanding, preferably spaced-apart fins or ridges 48 arranged in a semi-circle. To compensate for the weight of ridges 48, disc portion 47a is made thinner than disc portion 47b.

By virtue of the arrangement shown in FIGS. 9 and 10, disc 47 has a single pivot axis, extending along one of its diameters, without using a shaft. Due to the particular spacing arrangement between protrusions 45, abutment 24, and baffle plate 25, as well as the S cross-sectional shape of the disc, disc 47 cannot fall out of body 15. The operation of the valve of FIGS. 9 and 10 is similar to that described in connection with the valve of FIGS. 1–4.

An additional embodiment of the invention is shown in FIGS. 11 and 12. This embodiment is identical to the embodiment illustrated in FIGS. 5–8, with the exception of the formation of the pocket arrangement carried by disc 42. In place of the pocket arrangements 30a and 30b, of FIGS. 5–8, the arrangment of FIGS. 11 and 12 includes a pocket arrangement 30d comprising a series of upstanding, preferably spaced apart fins or ridges 51 arranged in a circle. It will be appreciated that ridges 51 are symmetrical with respect to any diameter of disc 42, and hence operation of the valve will not be affected regardless of the position to which disc 42 rotates in its own plane. Operation of the valve of FIGS. 11 and 12 is identical to that of FIGS. 5–8.

Figure 14:
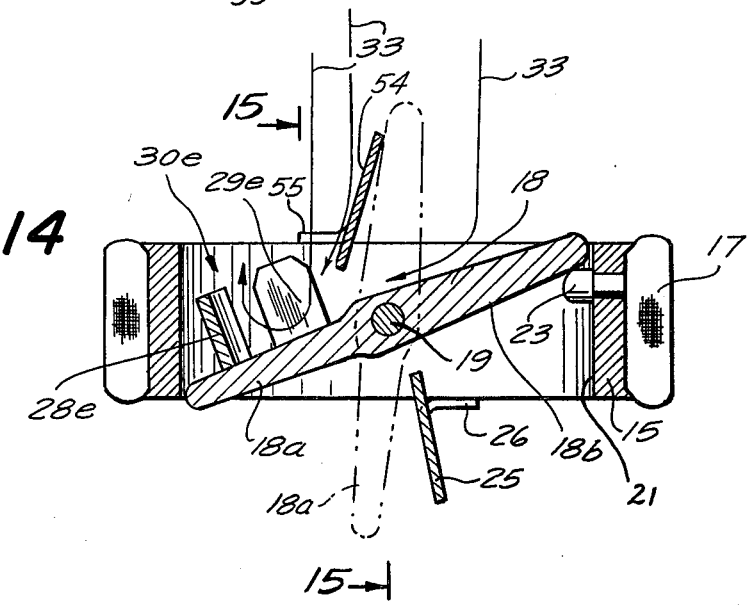
FIG. 14 is a vertical cross-sectional view taken along line 14—14 of FIG. 13.
Figure 15:
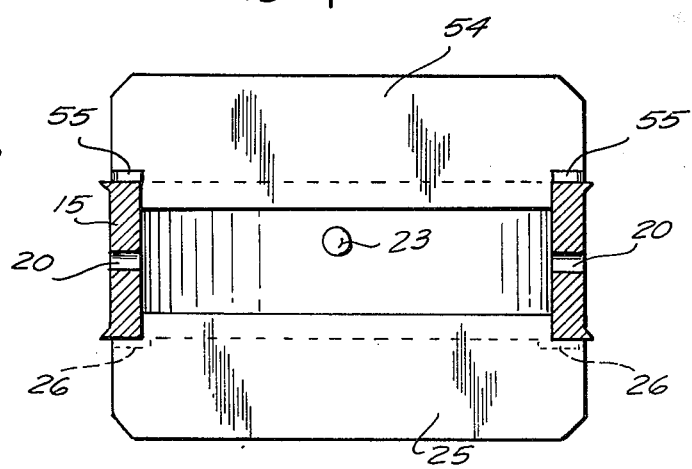
FIG. 15 is a vertical cross-sectional view taken along line 15—15, the disc and suture ring being removed for clarity.

Another embodiment of the invention is shown in FIGS. 13–15. The valve includes, as in the embodiment of FIGS. 1–4, an annular valve body 15 surrounded by a suture ring 17 and provided with a baffle plate 25, on its downstream end, and an abutment 23. In addition, body 15 is furnished with a second baffle plate 54 fixed to the upstream end of the body by tabs 55. Baffle plate 54 is parallel to the same diameter of body 15 to which baffle plate 25 is parallel, and baffle 54 is slightly spaced from that diameter on the side thereof opposite the side on which baffle 25 is spaced from that diameter. Furthermore, baffle plate 54 is arranged at an obtuse angle to the plane of valve body 15 on the disc portion 18a side of the valve body.

Disc 18 may be identical to the disc of the FIGS. 1–4 embodiment. The disc carries a pocket-like arrangement 30e similar to the pocket 30 of FIGS. 1–4. However, the ridges 28e and 29e of FIG. 13 are substantially shorter than the ridges 28 and 29 of FIGS. 1–4. This reduction in height of the pocket-forming ridges is made possible by the presence of baffle plate 54, which helps direct blood flow toward pocket 30e when the closed valve is to be opened, as indicated by arrows 33. In other words, the combination of baffle plate 54 and shorter ridges 28e and 29e yields the same results as the taller ridges 28 and 29 alone. The advantage of the shorter ridges 28e and 29e is that, when the valve is open, they offer less obstruction to blood flow through opening 21 than do the taller ridges 28 and 29 of FIGS. 1–4.

Furthermore, in this embodiment, no abutment comparable to abutment 24 of FIGS. 1–4 is necessary, since baffle plate 54 serves as such an abutment. In its open position, disc 18 engages baffle plate 54.

The invention has been shown and described in preferred form only, and by way of example, and many variations may be made in the invention which will still be comprised within its spirit. It is understood, therefore, that the invention is not limited to any specific form or embodiment except insofar as such limitations are included in the appended claims.

What is claimed is:

1. A prosthetic one-way heart valve comprising:
   a generally annular valve body having a central opening defining a blood flow passageway,
   a disc within said valve body and having a periphery substantially complementary to the periphery of said opening,
   means supporting said disc for pivotal movement with respect to said body about an axis extending substantially along a centerline of said disc,
   vane means projecting from one face of said disc in a direction opposite to the flow direction through the valve, said vane means being responsive to fluid flow in the flow direction of the valve for causing said disc to pivot to a position in which the valve is open, and
   baffle means carried by said valve body adjacent to the face of said disc opposite the face from which said vane means project, said baffle means extending across said opening and being arranged to direct fluid flowing in the no-flow direction of said valve against the portion of said disc which moves toward the flow direction when the valve opens, thereby pivoting said disc to a position in which the valve is closed.

2. A prosthetic one-way valve as defined in claim 1 wherein said body carries means for limiting the pivotal movement of said disc to an acute angle between a position in which it is arranged at a relatively small acute angle to the plane of said valve body and a position in which it is arranged at a relatively large acute angle to the plane of said valve body.

3. A prosthetic one-way valve as defined in claim 1 wherein the portions of said disc on opposite sides of said pivot axis are of substantially equal weight.

4. A prosthetic one-way valve as defined in claim 1 wherein the portions of said disc on opposite sides of said pivot axis are of substantially equal size.

5. A prosthetic one-way valve as defined in claim 1 including needle-pierceable means surrounding said body by means of which the valve can be sutured to a heart.

6. A prosthetic one-way valve as defined in claim 1 wherein said means for pivotally supporting said disc includes a shaft extending through said disc in the plane of the latter, the ends of said shaft being mounted in said valve body.

7. A prosthetic one-way valve as defined in claim 1 wherein said means for pivotally supporting said disc includes two pairs of protrusions projecting from said valve body into said central opening, said pairs being at diametrically opposed locations, and the peripheral edge of said disc being loosely accommodated between each of said pairs of protrusions.

8. A prosthetic one-way valve as defined in claim 7 including retaining fingers mounted on said valve body and projecting into the path of pivotal movement of said disc so as to limit that movement and prevent said disc and valve body from becoming disassembled.

9. A prosthetic one-way valve as defined in claim 7 wherein said disc is bent twice to provide two parallel but offset portions on opposite sides of said pivot axis joined by a central portion arranged at an angle to said two parallel portions, and a third protrusion associated with each of said pairs of protrusions for limiting the pivotal movement of said disc.

10. A prosthetic one-way valve as defined in claim 1 wherein said vane means is carried only by the portion of said disc which moves toward the flow direction when the valve opens.

11. A prosthetic one-way valve as defined in claim 1 wherein said vane means is carried by the portions of said disc on both sides of said pivot axis, said vane means being arranged symmetrically with respect to said pivot axis.

12. A prosthetic one-way valve as defined in claim 1 wherein said vane means comprises a plurality of upstanding ridges arranged at angles to each other so as to define a pocket for catching flowing fluid.

13. A prosthetic one-way valve as defined in claim 12 wherein said ridges are spaced from each other to define openings through which fluid can flow out of the pocket.

14. A prosthetic one-way valve as defined in claim 1 wherein said means for pivotally supporting said disc also support said disc for rotation in its own plane.

15. A prosthetic one-way valve as defined in claim 14 wherein said vane means is so arranged on said disc that it is symmetrical with respect to any pivot axis of said disc.

16. A prosthetic one-way vale as defined in claim 1 including additional baffle means carried by said valve body adjacent to the face of said disc from which said vane means project, said additional baffle means extending across said opening and being arranged to direct fluid flowing in the flow direction of the valve toward said vane means, thereby helping to pivot said disc to a position in which the valve is open.

* * * * *